United States Patent
Creaghan

(10) Patent No.: US 7,431,695 B1
(45) Date of Patent: Oct. 7, 2008

(54) NEONATAL TRANSILLUMINATOR APPARATUS

(75) Inventor: Frank Creaghan, Lafayette, LA (US)

(73) Assignee: Venoscope, LLC ( * ) Notice: Subject to any disclaimer, the term of this patent is extended or adjusted under 35 U.S.C. 154(b) by 308 days.

(21) Appl. No.: 11/195,321

(22) Filed: Aug. 2, 2005

Related U.S. Application Data

(60) Provisional application No. 60/598,457, filed on Aug. 3, 2004.

(51) Int. Cl.
*A61B 1/06* (2006.01)
(52) U.S. Cl. .................. 600/249; 362/231
(58) Field of Classification Search ........ 600/476, 600/310, 249; 362/230, 231, 800
See application file for complete search history.

(56) References Cited
U.S. PATENT DOCUMENTS 5,080,098 A * 1/1992 Willett et al. .......... 600/476
5,983,120 A * 11/1999 Groner et al. .......... 600/310
7,006,223 B2 * 2/2006 Mullani .................. 356/369

* cited by examiner

*Primary Examiner*—Eric F Winakur
*Assistant Examiner*—Katherine L Fernandez
(74) *Attorney, Agent, or Firm*—Garvey, Smith, Nehrbass & North, L.L.C.; Gregory C. Smith

(57) ABSTRACT

A transilluminator device for use with neonatal patients, which includes a power housing for providing power to the unit; a flexible cord, extending from the housing, and terminating in a small container for housing LED's; a plurality of red and white LED's containing the smaller housing, which are illuminated when power is provided to the LED's; the small housing positionable in the hands of a person, so that when a neonatal patient is placed in the person's hand the LED's will illuminate that portion of the neonatal person such as the arm, leg or other part of the anatomy in order to determine whether or not the physical conditions are normal or abnormal and to locate suitable veins for blood draws and IV therapy in an infant.

8 Claims, 2 Drawing Sheets

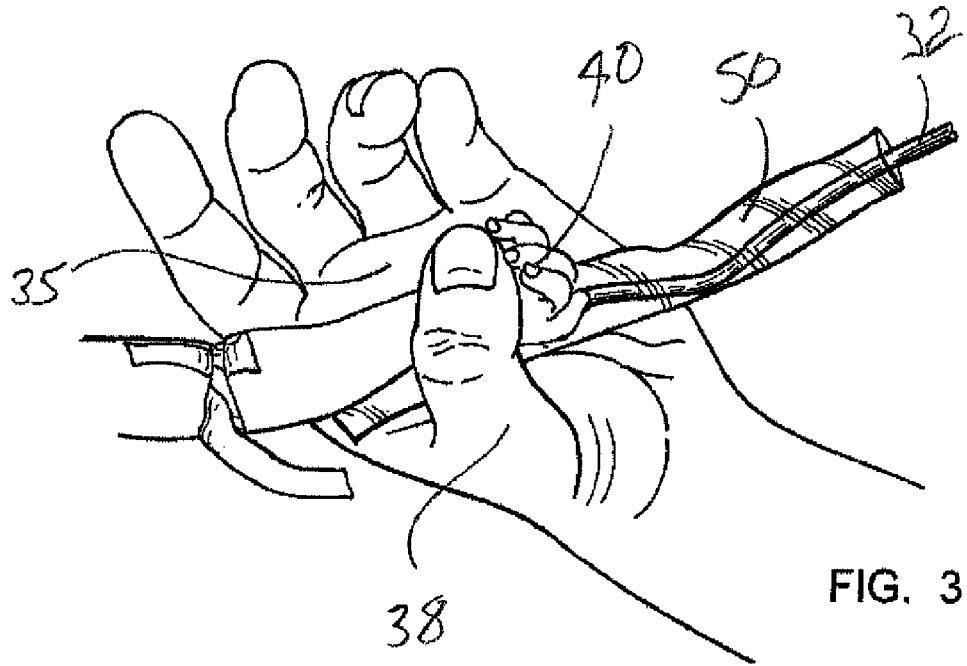
FIG. 3
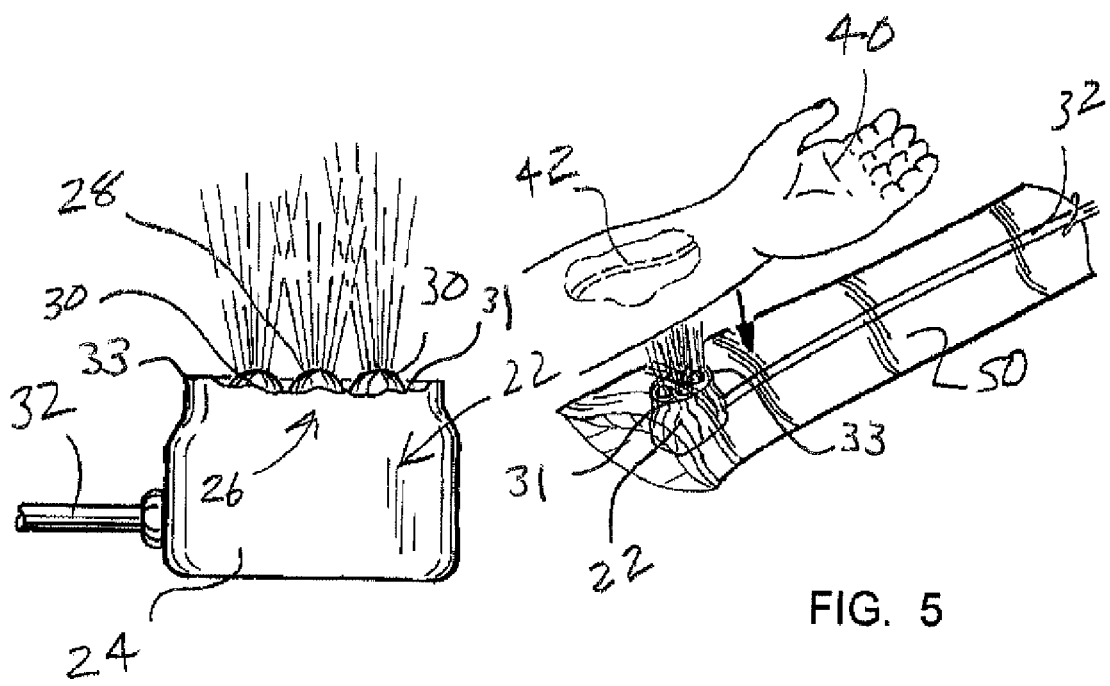
FIG. 4
FIG. 5

NEONATAL TRANSILLUMINATOR APPARATUS

CROSS-REFERENCE TO RELATED APPLICATIONS

Priority of U.S. Provisional Patent Application Ser. No. 60/598,457, filed Aug. 3, 2004, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The apparatus of the present invention relates to transilluminator devices. More particularly, the present invention relates to a neonatal transilluminator device using multiple LED lights with varying wavelengths which provides the location of veins of neonates or dark skinned adults.

2. General Background of the Invention

In the field of locating hard-to-find veins beneath the skin, a device has been developed which is defined as a transcutaneous illuminating apparatus which included a housing having a source of electrical energy provided therein, a support removably mounted on one end of the housing having a plurality of arms pivotally supported thereby at their proximate ends, each of the arms having mounted on its distal end illuminating lights, an electrical circuit including the source of power and the illuminating lights, a switch for selectively completing the circuit between the illuminating lights and the source of electrical energy thereby activating the illuminating lights, and rheostats provided in the circuit for selectively varying the intensity of each of the illuminating lights. This device, entitled "Transcutaneous intravenous illuminator" was originally patented under U.S. Pat. No. 4,619,249 in 1986. The '249 patent was reissued as RE 33,234. Additionally, the present inventor patented an ornamental design for an instrument for viewing subcutaneous venous structures, as design Pat. No. 362,910. These devices, although suitable for certain adults, are not user friendly when trying to examine newborn infants.

BRIEF SUMMARY OF THE INVENTION

The apparatus of the present invention solves the problems in the art in a simple and straightforward manner. What is provided is an apparatus for locating veins in a neonatal infant and pediatric patients which includes high intensity LED white and red lights with different wavelengths in order to illuminate the subcutaneous tissue. The red and white lights provide the contrast between the subcutaneous tissue which reflects light and the blood vessels which absorb light. The LED lights will not generate heat such that it will burn the infant and there is further included long clear disposable non-latex protective covers which prevent the spread of infection and protect the device from blood and other contaminants. The device further includes a small flexible cord and the ability to hold the light in the palm of the hand by one nurse. In this manner the infant arm or leg can be pressed up against the light in the hand of the nurse and the veins can be illuminated.

Therefore, it is the principal object of the present invention to provide a transilluminated device used to locate veins and arteries in neonatal infants in pediatric patients which allows the LED to be held in the palm of a hand in order to illuminate the infant arm or leg;

It is the further object of the present invention to provide a neonatal transilluminator device which is used by placing the light in the palm of the nurses hand and pulling the baby's hand over the light such that the veins are observable from the top while being illuminated from beneath;

It is a further object of the present invention to provide a neonatal transilluminator device which can be used to check for fluid on the brain, hydrocephalic, by placing the light on the scalp and observing whether there is a large glowing area indicating the light being reflected by fluid;

It is a further object of the present invention to provide a neonatal transilluminator device which utilizes a small flexible cord with the LED's at the end of the cord in order to allow a person to hold the light in the palm of the hand while illuminating the veins of an infant or neonatal patient;

It is a further object of the present invention to provide a neonatal transilluminator device which can be used to check for collapsed lungs, pneumothorax, by placing the light on the side of the chest wall and observing whether there is a large glowing area in the chest region indicating reflection of the light within the pleural space;

It is a further object of the present invention to provide a neonatal transilluminator device which is utilized to locate suitable veins for blood draws and IV therapy in an infant.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 3 illustrates the present invention utilized with a neonatal infant;

FIG. 4 illustrates a partial view of the illumination portion of the present invention; and FIG. 5 illustrates a cutaway view of the us of the present invention as illustrated in FIG. 3.

DETAILED DESCRIPTION OF THE INVENTION

Figure 1:
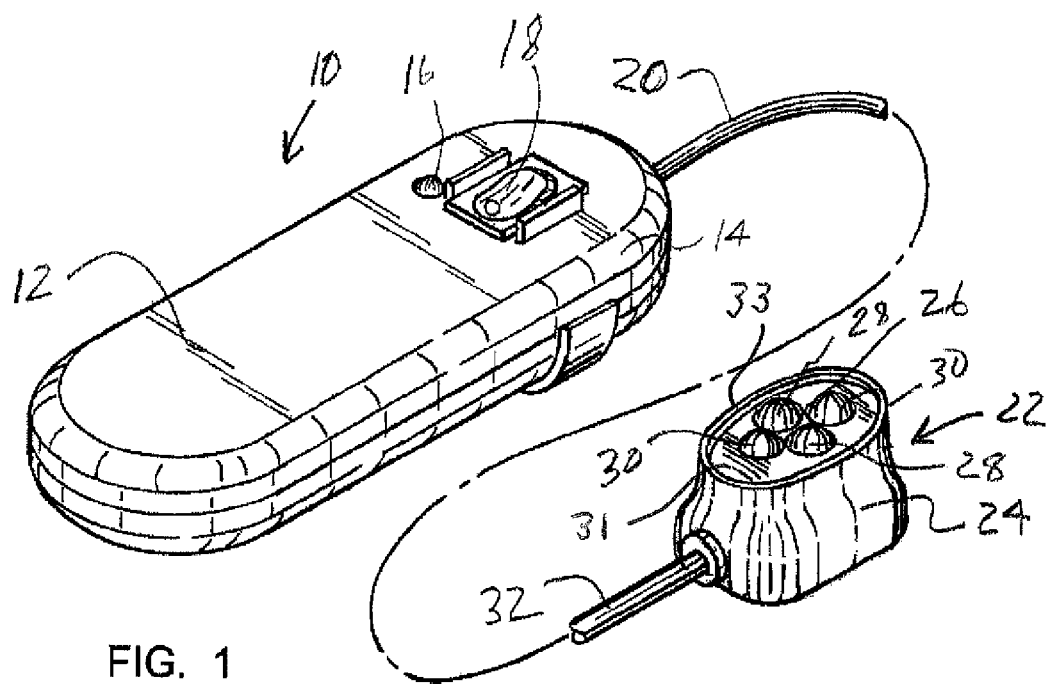
FIG. 1 illustrates an overall view of the preferred embodiment of the device of the present invention.

Reference is made to FIGS. 1 through 5 which illustrate the preferred embodiment of the apparatus of the present invention. What is provided is a neonatal transilluminator apparatus 10, which includes a power housing 12, which includes an exterior cover portion 14, which houses a plurality of batteries (not illustrated) therein, such as 3 AA batteries, and includes a low battery indicator LED light 16 and an on/off switch 18. There is further provided a flexible cord 20, preferably 30 inches in length, which extends from one end of the housing 12, and on a second end includes the illuminator portion 22, which comprises a small rectangular housing 24, having a plurality of LED's 26, preferably with at least two white LED's 28, and two red LED's 30, with the white and red LED's 28, 30 providing a contrast between the subcutaneous tissue which reflects light and the blood vessels which absorb light. As seen in FIG. 1, there is further included a face 31 on the illuminated portion 22 wherein the LEDs 28 and 30 protrude therefrom. The face 31 is surrounded by a raised edge 33 which is also clearly seen in FIGS. 4 and 5. For purposes of construction, at this state in the art, LEDs are the light source available for the best mode, although if other more suitable light sources are developed, these may be used in the place of the LEDS.

Figure 2:
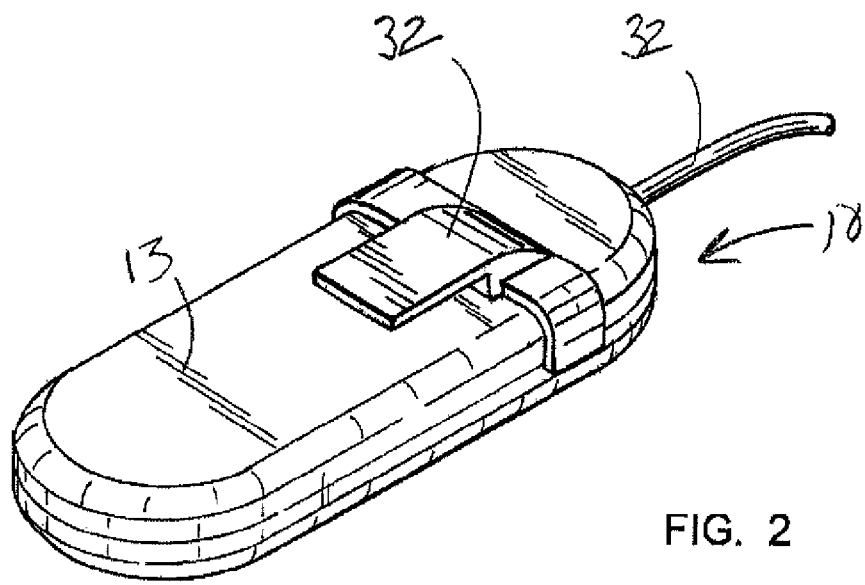
FIG. 2 illustrates a partial view of the backside of the power housing of the present invention.

Reference is made to FIG. 2, which illustrates the rear face 13 of the power housing 12, which houses the batteries, and includes a belt clip 32 attached to the housing 12, so that the power housing 12 may be attached to the nurses pocket or attached to the baby's bed while being used by the nurse or doctor. The LED housing 24 houses the red and white LED lights in a small compact case such that it can fit in the palm of the hand, as illustrated in FIG. 3, which will be discussed.

In the use of the apparatus 10, as illustrated in FIG. 3, the apparatus 10 is used on neonates by placing the LED housing 24 in the palm 35 of the nurses hand 38 and pulling the neonatal infant's hand 40 over the LEDs 26, 28, turning the On/OFF switch to the On position, so that the LEDs 26, 28 become energized and emit light, as seen in FIG. 4. When this occurs, the veins 42 are observable from the top while transilluminated from beneath, as illustrated in FIG. 5. It should be noted also, as seen in FIG. 3, that the LED portion is housed within a plastic sheath 50 to avoid contamination when in use.

In its preferred embodiment the apparatus may also be used on all parts of the infants anatomy, including but not limited to the forearm, scalp and the foot; to check for collapsed lungs (pneumothorax), by placing the LEDS 26, 28 on the side of the chest and observing a large glowing area which indicates a collapsed lung, or opposite no glowing area which indicates that the lung is inflated. It can also be used to check for fluid on the brain, (hydrocephalic), by placing the LEDs 26, 28 on the scalp and observing whether there is a large glowing area indicating the light being reflected by the fluid. No glowing area would indicate the absence of fluids. Also, as stated earlier, the neonatal transilluminator device would be utilized to locate suitable veins for blood draws and IV therapy in an infant.

Another point of novelty, which is not found in the prior art, allows the device to be used with very tiny neonatal infants. Because the LED's 26, 28 are contained within the small housing 24 at the end of the flexible cord 20, one can hold the LED housing 24 in one's hand when undertaking the transilluminating function, while the main power portion, on the end of the cord 20, remains attached to a remote location. This frees both hands of the nurse or care giver to secure the infant's anatomy correctly for proper readings.

In the prior art, as discussed in the Background of the Invention, the LED's in the apparatus were at the end of two inflexible arms, which would not allow one to hold the LED's in one's hands but one would simply place the LED's on the portion of the skin that was being illuminated. This was impractical for neonatal patients or young children since it did not allow the person who used the device to hold the patient in one hand and the device in the same hand simultaneously so as to get a clear reading of the position of the veins or other structures being illuminated.

The following is a list of suitable parts and materials for the various elements of the preferred embodiment of the present invention.

| PARTS LIST | |
|---|---|
| Parts Number | Description |
| 10 | transilluminator apparatus |
| 12 | power housing |
| 13 | rear face |
| 14 | cover portion |
| 16 | LED indicator light |
| 18 | ON/OFF switch |
| 20 | flexible cord |
| 22 | illuminator portion |
| 24 | rectangular housing |
| 26 | LEDs |
| 28 | white LEDs |
| 30 | red LEDs |
| 32 | belt clip |
| 35 | palm |
| 38 | hand |
| 40 | infant's hand |
| 42 | veins |
| 50 | plastic sheath |

The foregoing embodiments are presented by way of example only; the scope of the present invention is to be limited only by the following claims.

The invention claimed is:

1. A transilluminator device for use with neonatal patients, comprising:
   a) a power housing for providing power to the device;
   b) an illuminator portion, comprising a face portion including a plurality of LEDs extending a height above the face portion wherein said LEDs consist of red and white LEDs as the principal source of illumination which are arranged to provide contrast between subcutaneous tissue which reflects light and blood vessels which absorb light when transilluminating a patient, the LEDs receiving power from the power housing;
   c) a raised edge surrounding the face portion to a height substantially the height of the red and white LEDs to capture light emitted by the red and white LEDs;
   d) a flexible cord, extending from the power housing, and terminating in the illuminator portion for illuminating the LEDs when power is provided to the LEDs; and
   e) the illuminator portion positionable in the hands of a person, so that the LEDs on the face of the illuminator portion with the raised edge will illuminate that portion of the neonatal patient beneath the face portion, such as the arm, leg or other part of the anatomy, in order to determine whether or not the physical conditions are normal or abnormal; while the power housing remains at a remote location.

2. The device of claim 1, wherein the power housing includes a clip.

3. The device in claim 1, wherein the power housing is clipped to a belt or other structure when the LEDs are used in the illumination process.

4. The device in claim 1, further comprising a clear, plastic sheath for shielding the LEDs from contact with the skin of the infant when in use.

5. A transilluminator apparatus for use with neonatal patients, comprising:
   a) a power housing containing batteries for providing power to the apparatus;
   b) a flexible cord, extending from the power housing, and terminating in a small portion;
   c) a plurality of LEDs wherein said LEDs consist of red and white LEDs as the principal source of illumination contained on a face of the small portion and extending a height above the face which are arranged to provide a contrast between subcutaneous tissue which reflects light and blood vessels which absorb light when transilluminating a patient, when power is provided to the LEDs;

d) a raised edge surrounding the face portion to a height substantially the height of the red and white LEDs to capture light emitted by the red and white LEDs; and e) the small portion positionable in the hands of a person, so that the LEDs on the face portion with the raised edge will illuminate that portion of the neonatal patient beneath the face portion, such as the arm, leg or other part of the anatomy in order to determine whether or not the physical conditions are normal or abnormal, while the power housing is clipped to a remote structure.

6. The apparatus in claim 5, wherein the cord is sufficiently long to allow the power housing to remain remotely positioned from the LEDs to allow a nurse to position the LEDs on the infant with one hand.

7. A transilluminator apparatus for use with patients, comprising:

a) a power housing for providing power to the apparatus positionable at a remote location;

b) a flexible cord, extending from the power housing, and terminating in a small container for housing a plurality of LEDs;

c) the small container comprising a face portion, the face portion including a plurality of LEDs extending a height above the face portion wherein said LEDs consist of red and white LEDs as the principal source of illumination which are arranged to provide contrast between subcutaneous tissue which reflects light and blood vessels which absorb light when transilluminating a patient when power is provided to the LEDs;

d) a raised edge surrounding the face portion to a height substantially the height of the red and white LEDs to capture light emitted by the red and white LEDs; and e) the small container positionable in the hands of a person, so that the LEDs on the face portion with the raised edge will illuminate that portion of the patient beneath the face portion, such as the arm, leg or other part of the anatomy to provide a contrast between subcutaneous tissue which reflects light and blood vessels which absorb light in order to determine whether or not the physical conditions are normal or abnormal.

8. The apparatus in claim 7, further comprising a clear, plastic sheath for shielding the small container from contact with the skin of an infant when in use.

* * * * *